US012387834B2

(12) United States Patent
Schrörs et al.

(10) Patent No.: US 12,387,834 B2
(45) Date of Patent: Aug. 12, 2025

(54) MEDICAL DEVICE AND METHOD OF COMMUNICATION FOR A MEDICAL DEVICE

(71) Applicant: FRESENIUS MEDICAL CARE DEUTSCHLAND GMBH, Bad Homburg (DE)

(72) Inventors: Alexander Schrörs, Frankfurt a.M. (DE); Robert Schröder, Darmstadt (DE); Lucas Keune, Aachen (DE); Lena Schreiber, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 498 days.

(21) Appl. No.: 17/909,779

(22) PCT Filed: Mar. 11, 2021

(86) PCT No.: PCT/EP2021/056127
§ 371 (c)(1),
(2) Date: Sep. 7, 2022

(87) PCT Pub. No.: WO2021/180827
PCT Pub. Date: Sep. 16, 2021

(65) Prior Publication Data
US 2023/0114894 A1 Apr. 13, 2023

(30) Foreign Application Priority Data
Mar. 11, 2020 (DE) ..................... 10 2020 106 643.0

(51) Int. Cl.
*G16H 20/40* (2018.01)
*A61M 1/14* (2006.01)
*G16H 40/63* (2018.01)

(52) U.S. Cl.
CPC .............. *G16H 20/40* (2018.01); *A61M 1/14* (2013.01); *G16H 40/63* (2018.01); *A61M 2205/3576* (2013.01); *A61M 2205/581* (2013.01); *A61M 2205/6018* (2013.01)

(58) Field of Classification Search
CPC ............ A61M 1/14; A61M 2205/3576; A61M 2205/581; A61M 2205/6018; G16H 20/40; G16H 40/63
See application file for complete search history.

(56) References Cited

U.S. PATENT DOCUMENTS

| | | |
|---|---|---|
| 5,113,859 A | 5/1992 | Funke |
| 8,301,232 B2 | 10/2012 | Albert et al. |
| 2001/0012955 A1 | 8/2001 | Goedeke et al. |
| 2011/0301439 A1 | 12/2011 | Albert et al. |
| 2016/0284198 A1 | 9/2016 | Tarn et al. |

FOREIGN PATENT DOCUMENTS

EP 2 740 413 A1 6/2014

*Primary Examiner* — John Kim
(74) *Attorney, Agent, or Firm* — Kilyk & Bowersox, P.L.L.C.

(57) ABSTRACT

The present invention relates to a medical device, in particular a device for extracorporeal blood treatment, having an output unit for outputting system sounds for communication with a user, wherein the output unit is additionally adapted to transmit message sounds for communication with at least one other apparatus.

17 Claims, No Drawings

MEDICAL DEVICE AND METHOD OF COMMUNICATION FOR A MEDICAL DEVICE

The present invention relates to a medical device and to a method of communication for a medical device and preferably for at least one further different apparatus.

Conventional medical devices such as extracorporeal blood treatment devices, in particular dialysis machines, are characterized by an only limited communication capability.

This in particular results in challenges in situations in which a plurality of such medical devices have to be operated in a coordinated manner.

In a dialysis station, for example, a plurality of dialysis machines are, for instance, typically operated in a time synchronized manner. Since all the devices should carry out the same pre-preparation processes, post-preparation processes and operating processes as simultaneously as possible, a synchronization of the devices is required.

The operation of a group of devices is, however, conventionally implemented as a sequencing of manual process repetitions without a communication possibility between the devices. The personnel has to run from device to device for this purpose and has to initiate the same process at every single device by a manual input. This not only results in a physical strain (running distances) and in a mental strain (process repetition) of the personnel, but also in unwanted delays in the operating procedure.

The personnel typically initiates all the machines individually after one another before the start of treatment operation and then, after the ending of the individual preparation steps by the respective device, triggers the next process in each device. Since the individual processes can take up different amounts of time in dependence on the device, the resulting procedure is often uncoordinated and inefficient.

Different solution approaches are known from the prior art to eliminate these problems based on a lack of communication capability of the medical devices.

For example, the communication capability should be increased in that medical devices, e.g. dialysis machines, are equipped or upgraded with a network interface via which data can be transmitted, e.g. over the intranet, from/to the device.

With older devices that make up the larger part of all the dialysis machines in use, this network interface has to be retrofitted, which represents a considerable effort in technical, regulatory, and financial terms and is not always possible.

It is thus the underlying object of the present invention to alleviate or even to fully eliminate the problems known in the prior art. A medical device having an improved communication capability and a method for communication of a medical device with other devices or also with non-medical apparatus should specifically be provided This object is achieved by a medical device in accordance with claim 1 and by a method in accordance with claim 9.

A medical device in accordance with the invention, in particular a device for extracorporeal blood treatment, has an output unit for outputting system sounds for communication with a user, with the output unit additionally being adapted to transmit message sounds for communication with at least one other apparatus.

In other words, the existing hardware, that is, the output unit, is used to also carry out communication with other medical devices or also non-medical apparatus in addition to the communication with a user. The necessity for a complex and/or expensive upgrade is dispensed with by this double use of the existing output unit.

The fact is utilized here that a large number of conventional dialysis machines are equipped with an output unit, for example in the form of a loudspeaker or loudspeakers. This is often prescribed by regulations so that the personnel can be alerted by sound.

So that the function of the loudspeaker can be ensured, the devices are also equipped with a reception unit, in particular with a microphone, that is inter alia sensitive to all system sounds.

In other words, in accordance with the invention, these already existing units (microphone and loudspeakers) and the already established system sounds (e.g. information sounds, notification sounds, alarm sounds, test sounds) can thus be used to implement an additional communication interface without an upgrading/retrofitting of the devices.

For this purpose, in accordance with the invention, data that are to be communicated between the devices are encrypted and are encoded as a sound sequence (also called a message sound). These encrypted messages are preferably transmitted simultaneously with the emitted system sounds by the same output unit or by the same loudspeaker and are received by the reception unit (e.g. microphone) of another device.

The frequency of the message sound is thus preferably put into relation with the frequency of the system sound such that the additional message/the message sound cannot be perceived by the human ear. This method serves the masking of the message sound.

A different kind of masking that can also be used is temporal masking in which an additional message sound, that is preferably short and quiet relative to the system sound and that contains the additional data message is appended at the end of the system sound.

It has proved to be advantageous in practice if, with a medical device in accordance with the invention, the database of the system sounds stored on the device is expanded for this purpose by the message sounds and their adaptation to the masking within any desired system sound. In other words, the database of a medical device in accordance with the invention thus does not only contain the conventional system sounds, but also a number of message sounds. In addition, the medical device has corresponding software that enables the device to correspondingly encrypt the message sounds or to decrypt and/or to mask or unmask received message sounds.

The system sounds output by a medical device in accordance with the invention are preferably perceptible to human hearing and the message sounds, alone or in combination with the system sounds, are not perceptible to human hearing so that users are not disturbed by the communication between the devices and apparatus or do not even perceive it.

The reception unit of a medical device in accordance with the invention is preferably adapted to receive and preferably to decrypt or unmask the message sounds of at least one other apparatus that is a medical or also a non-medical device (e.g. a cellular phone or a tablet).

Data that can be contained in such a masked message or message sound, individually or in combination, are inter alia:

a device ID, a location ID, an ID of an error message, an ID of an ongoing and/or last ended and/or next upcoming process, a message with respect to the status of the process, e.g. data with respect to the time progress of the order of a queue of a plurality of devices or an actuator/trigger for action instructions for other devices. This list is, however, only exemplary and the type of data transmitted is completely as desired.

All of these data or all of this information can, including redundancies in accordance with the invention, be encoded within a message sound that does not exceed common system sounds in time.

Sound sequences can also additionally be included that do not occur as part of naturally generated sounds to avoid confusion of the message sound with environmental noise.

The reception unit or the microphone of a device records both portions, the system sound and the preferably masked message sound, of the emitted sound and the two portions are preferably separately processed within a device computer (that preferably has an evaluation unit and a control unit) of the receiving device. The system sound is processed as conventionally usual, e.g. as a self-test, and the masked notification sound is decoded and then processed in dependence on the content.

In accordance with an advantageous embodiment, a control unit of a medical device in accordance with the invention is adapted to control the medical device in agreement with a message sound received by the reception unit.

The control unit preferably controls the medical device to at least partially output the received message sound, to initiate or end a predetermined process preferably stored in a database, to output data, in particular data with respect to the device status, as a preferably masked message sound, to switch off the reception unit or to ignore message sounds or to output a sound perceptible to human hearing for the purpose of emitting an alarm. This list is, however, only exemplary and other actions are conceivable.

To perform such actions, the software of the device-controlling computer or of the control unit of a medical device in accordance with the invention is expanded. If an action instruction is part of the masked message, the receiving device performs it. Possible actions (and corresponding triggering messages) are stored in a database in the memory of the device.

All the action instructions can be conditionally correlated with operating parameters of the receiving devices and/or can be correlated in time, i.e. an action instruction should be performed after the elapse of a specific time after reception of the message and/or when the receiving device is in a specific status.

The transmission and reception of the masked sounds in conjunction with the actions subsequent to the reception enables a multi-stage communication between a plurality of devices without them having to be modified or upgraded at the hardware side. The communication between the devices should preferably run in parallel with the already established standard sounds/system sounds, but can also take place unmasked and/or independently of the standard sounds/system sounds as required.

In a medical device in accordance with the invention, the output unit is therefore preferably adapted to simultaneously emit the system sounds and the message sounds so that the message sounds are transmitted in a masked manner.

A control unit can in particular be provided at the side of the medical device that sets the frequency of the message sounds to be transmitted by the output unit relative to the frequency of the system sounds to be transmitted by the output unit such that a masking of the message sounds takes place.

In accordance with an advantageous aspect of the invention, the output unit is adapted to output the message sounds directly before or after the system sounds or within system sound breaks.

The control unit is preferably adapted to encrypt or mask the message sounds to be output before output.

A further aspect of the invention relates to a method of communication of a medical device with at least one other apparatus comprising the steps:
 outputting a system sound preferably perceptible to human hearing, preferably by means of an output unit of the medical device and/or of the at least one other apparatus; and
 outputting a message sound preferably not perceptible to human hearing, preferably by means of the same output unit of the medical device and/or of the at least one other apparatus, with the message sound being adapted to be received by the medical device and/or the at least one other apparatus.

The method can be used for communication between a plurality of medical devices or for communication of a medical device with at least one other, preferably non-medical apparatus.

In addition to messages between one another, the masked sounds of the devices can in other words thus also be perceived by a non-medical communication device or by an apparatus (e.g. a cellular telephone) having a microphone, a loudspeaker, and a conventional communication possibility (e.g. by WiFi).

The non-medical apparatus is ideally positioned in the environment of the medical devices, e.g. in the treatment room, such that it can perceive the sounds of all the medical devices located in the room without interference.

The non-medical apparatus is preferably also able to produce sounds that are generated by the medical devices or treatment devices. The non-medical apparatus can communicate with other non-medical devices, e.g. with a cellular telephone of the carers, by the network connection. The personnel can thereby be informed of the status of device processes, any warnings, etc. even when not in hearing/visible range of the treatment devices.

Conversely, the personnel can also communicate action instructions to a non-medical apparatus located in the environment of the medical devices by input at the non-medical apparatus/at the cellular phone, said action instructions then being transmitted by sound to individual medical devices. A direct communication between a communication device (e.g. a cellular phone) of the carers and the medical devices is also conceivable.

The method preferably furthermore comprises the step:
 masking the message sound by the system sound, preferably by means of a frequency-based masking or a temporal masking.

The masking provides the advantage that human users are not distracted or disturbed by the communication of the devices between one another.

In accordance with an advantageous embodiment, the method furthermore comprises the steps:
 evaluating the message sound, preferably by means of an evaluation unit at the side of the medical device and/or of the at least one other apparatus; and
 performing a control command encoded in the message sound by means of a control unit at the side of the medical device and/or of the at least one other apparatus.

In this embodiment, the receiving device is caused by the message sound, as described above, to perform a predetermined action stored in a database.

A further aspect of the invention relates to a system of at least one medical device in accordance with the invention and at least one other apparatus, in particular a non-medical communication apparatus, wherein the system is preferably adapted to permit a communication in accordance with a method in accordance with the invention.

In such a system, the at least one other apparatus preferably has a reception unit, an output unit, and preferably a unit for a network connection and is preferably a cellular phone, a computer, or a tablet computer.

Another aspect of the invention relates to a computer program product for upgrading a conventional medical device, in particular an extracorporeal blood treatment apparatus, particularly a dialysis machine, for executing a method in accordance with the invention, wherein the computer program product includes instructions that, when they are read out of a conventional medical device, enable it to perform a method in accordance with the invention.

In other words, a computer program product in accordance with the invention contains instructions by means of which a conventional medical device can be upgraded or retrofitted to a medical device in accordance with the invention.

The computer program product can be provided, for example, on a data carrier (USB stick, CD, etc.). Alternatively, the computer program product can also be provided in the cloud so that the program stored in the cloud can be made use of for upgrading a specific medical device in a targeted manner to upgrade this device.

Further features, effects, and advantages of the present invention result from the following description of preferred, non-restrictive embodiments.

Dialysis machines should be put into a position to communicate with one another or with further external devices in that information is embedded in the system sounds inaudibly for the human ear.

Since the system sounds of a dialysis machine have to be very loud due to the demands of standards, good masking properties on the adjacent "frequency bands" result.

In this respect, system sounds mean all the conventionally emitted sounds of a medical device, e.g. of a dialysis machine, that is e.g. information sounds, notification sounds, and alarm sounds. Even the test sound in the T1 test can be used.

An application possibility of the present invention relates to synchronized processes with a plurality of dialysis machines.

In this respect, information in notification sounds can e.g. be used to control a group of devices located e.g. in the same room, in a synchronized manner, starting from the switching on of all the devices, together through the upgrading and preparation up to the treatment.

This is particularly interesting when the different devices remain in the individual preparation steps for different lengths of time due to different setup settings or due to different treatment methods.

The work of the carers is thereby considerably facilitated if the same actions always had to be carried out at all the devices at the same time or almost simultaneously.

The synchronization takes place in this respect such that the devices inter alia send their IDs and their locations to all the devices in the environment (identification notification) at the start, i.e. with the function test, with a preferably masked message sound. It is only important that all the devices are switched on when the identification notifications sound so that all the devices can receive them.

Alternatively, a synchronization takes place at the start. In this respect, all the devices send a specific signal and receive incoming sounds. Subsequently, which devices and also how many other devices are connected to and synchronized with each device is respectively stored in the devices.

In other words, all the devices so-to-say know which other devices are in a room with them. It would be necessary for this purpose to communicate its location, e.g. on setup, to a device so that it can transmit this.

A further possibility of recognizing devices in direct proximity would be a quantitative analysis of the signal amplitude and signal frequency in the message sounds received by the surrounding devices. A damping through walls and other partitions would change the signal amplitude and the signal frequency.

Information sent as part of a preferably masked message sound could have the following appearance: <Device xy, in room xyz, treatment method CVVxyz, notification #abcd (e.g. start filling)>

A next preparation step would then only be started if all the devices had reached the status required for this purpose, e.g. if all the devices had passed the T1 test (and transmit a corresponding signal) and could start with the upgrade, or all the devices are upgraded and could start with the filling.

For this purpose, the devices have to have noted which partner devices are in the room so that they know whether all the devices have reached the next step. Such a "noting" takes place as a storage of corresponding information in a database. For this purpose, the devices would have to know or have stored which steps are performed in the different treatment methods as part of the preparation.

As soon as a device has reached a status, it transmits a one-time message sound "I have reached the status" and is then quiet. If all the devices have reached this status, the last device outputs the normal notification sound or system sound and a user is aware that all the devices have reached the same status and that the user can perform the next action.

In general, a time restriction could also be provided so that, if the preparation time at one device takes longer, the remaining devices are not also affected by the delay. For example, a time interval is fixed in this respect in which a device has to give a notification at the end of a step and, if this is no longer the case, a further interval is waited again and the next step is then started, possibly without the delayed device.

If a device enters into an error state, it can simply communicate it to the other devices via a message sound. Devices can thereby dynamically register and unregister at or from the common process.

The affected device furthermore preferably outputs an audible signal sound/alarm sound to call the user. If the delay time for remedying the alarm does not exceed the fixed time interval, the device can also again enter into the synchronization.

Devices can here estimate whether another device is in front or behind them in the process.

In this manner, the devices could wait for one another and could be brought into the treatment with less thinking effort of the carers. In principle, a plurality of instances of one device could be brought into the treatment in a figurative sense (object-oriented programming).

In accordance with an alternative solution, provision could also be made that on an input, e.g. on the actuation of a control panel, at one device, the other devices are also started if they are at the same point in the process without an error. This would mean that on the actuation of a control panel at one device, a user could simultaneously confirm the same notification at all the devices. This command of one device to all participating devices can also be communicated in a message sound.

A further application possibility relates to the information of the carers via cellular phone. A further application possibility of information transmission via message sounds comprises the fact that the carers could likewise record and evaluate these sounds by means of their cellular phones.

It could thereby be communicated e.g. that the device xy in the room xyz is just outputting the notification or the status #abc. The personnel would know the status the dialysis machines are just in without a physical presence in the room.

A carer would therefore not only see that the dialysis machine xy is flashing red from a long way away; he could also see the event on the basis of which it is outputting an alarm.

A further application possibility relates to the information of the carers via a network. In this respect, one or more additional devices (non-medical apparatus or communication devices), e.g. also cellular phones, equipped with a microphone, set up at central positions at the ward, could record the system sounds and the further information of the dialysis machines, e.g. the message sounds, and could feed them into a network and could thus make the information accessible to the carers beyond all the rooms.

Human hearing comprises a lowest audible frequency of approximately 20 Hertz; the highest audible frequency amounts to a maximum of 20 kHz depending on the person's age. The audibility threshold depends on the frequency; the perception sensitivity is at the highest at approximately 4 kHz. The message sounds used can be inaudible or audible for the human ear.

In general, message sounds could be output in the inaudible frequency range. In some hardware configurations, only audible sounds can be considered. These generally audible sounds can nevertheless be made inaudible for the human ear (masking). Two types of masking are known:

On the one hand, sounds in the middle frequency range can simultaneously be masked by sounds in the low frequency range. This phenomenon is caused by the human hearing anatomy.

On the other hand, there is the time masking in which a further relatively quieter sound can no longer be perceived after the end of a relatively loud sound.

A microphone can, however, in contrast, perceive these frequencies and thus different frequency bands of different signal power and thus SNR (signal to noise ratio) can be fixed by corresponding band passes.

Message content can be placed in the message sound with amplitude or frequency modulation.

In general, a protocol similar to the CAN bus could be conceivable in the communication. There is a prioritization of the messages, i.e. the messages have IDs that are prioritized. This is necessary since all the devices "broadcast"/transmit on the same "bus", i.e. on the same frequency/line. This system has the advantage that frequencies can be identified that are at least partially unoccupied via which the devices could communicate.

Conversely, a special frequency could alternatively be issued to each device via a master.

A checksum should furthermore also be present after reception of a message sound so that the message can be examined for interference. The checksum is an example of a verification step of a received message.

If in addition an identification identifier is transmitted with the message sound over a frequency, all the devices know which device may transmit and which has to remain silent. That means that the useful content/messages can then be transmitted in further frequencies to transmit more data faster than simply over the sound.

Different transmission rates (BAUD rates) on different frequencies are possible here. A maximum distance of the machines or devices results from the maximum strength of the transmitted signals in which range the devices can communicate over a maximum distance from one another.

To secure the communication process against manipulations, the data should advantageously be encrypted prior to the communication. This increases the security of the communication together with a system for authentication.

The invention claimed is:

1. A medical device for extracorporeal blood treatment, having an output unit configured for simultaneously outputting system sounds, as an output, for communication with a user, and transmitting message sounds for communication with at least one other apparatus, wherein
   the system sounds are perceptible to human hearing, and
   the message sounds comprise data that is encrypted and encoded as sound sequences that are not perceptible to human hearing.

2. The medical device in accordance with claim 1, further comprising a reception unit that is configured to receive and to decrypt the second message sounds from at least one other apparatus.

3. The medical device in accordance with claim 2, wherein the control unit controls the medical device to at least partially output the received message sound; to initiate or end a predetermined process stored in a database; to output data pertaining to a status of the medical device as a masked message sound; to switch off the reception unit; to ignore message sounds; and to output a sound perceptible to human hearing for the purpose of emitting an alarm.

4. The medical device in accordance with claim 1, further comprising a control unit and a reception unit, wherein the control unit is adapted to control the medical device in agreement with a second message sound received by the reception unit.

5. The medical device in accordance with claim 1, wherein the output unit is adapted to output the message sounds directly before outputting the system sounds.

6. The medical device in accordance with claim 1, further comprising a control unit, wherein the control unit is adapted to encrypt the message sounds to be output prior to the output.

7. The medical device in accordance with claim 1, wherein the output unit is adapted to output the message sounds after outputting the system sounds.

8. The medical device in accordance with claim 1, wherein the output unit is adapted to output the message sounds within system sound breaks.

9. A medical device for extracorporeal blood treatment, having an output unit for outputting system sounds for communication with a user, wherein
   the output unit is additionally adapted to transmit message sounds for communication with at least one other apparatus, and
   the output unit is adapted to simultaneously emit the system sounds and the message sounds so that the message sounds are transmitted in a masked manner.

10. A medical device for extracorporeal blood treatment, comprising an output unit for outputting system sounds for communication with a user, and a control unit, wherein the output unit is configured to transmit message sounds for communication with at least one other apparatus, and the control unit sets the frequency of the message sounds to be transmitted by the output unit, relative to the frequency of the system sounds to be transmitted by the output unit, such that a masking of the message sounds takes place.

11. A method of communication of a medical device with at least one other apparatus comprising the steps of simultaneously:

outputting a system sound that is perceptible to human hearing, by means of an output unit of the medical device and/or of the at least one other apparatus; and outputting a message sound that is not perceptible to human hearing, by the same output unit that generated the system sound, wherein the message sound comprises data that are encrypted and are encoded as a sound sequence and is configured to be received by the medical device and/or the at least one other apparatus.

12. The method in accordance with claim 11, further comprising the steps of:

evaluating the message sound by means of an evaluation unit at the side of the medical device and/or of the at least one other apparatus; and performing a control command encoded in the message sound by means of a control unit at the side of the medical device and/or of the at least one other apparatus.

13. A method of communication of a medical device with at least one other apparatus comprising the steps of:

outputting a system sound perceptible to human hearing, by means of an output unit of the medical device and/or of the at least one other apparatus;

outputting a message sound that is not perceptible to human hearing, by means of the same output unit of the medical device and/or of the at least one other apparatus, with the message sound being adapted to be received by the medical device and/or the at least one other apparatus; and masking the message sound by the system sound by means of a frequency-based masking or a temporal masking.

14. A system comprising a device for extracorporeal blood treatment and a non-medical communication apparatus, wherein the system has an output unit for outputting system sounds for communication with a user, the output unit is configured to transmit message sounds for communication with the non-medical communication apparatus, and the system is configured to perform a communication in accordance with the method of claim 11.

15. The system in accordance with claim 14, wherein the non-medical communication apparatus has a reception unit, an output unit, and a unit for a network connection, and comprises a cellular phone, a computer, or a tablet computer.

16. A computer program product for upgrading an extracorporeal blood treatment apparatus, so that the extracorporeal blood treatment apparatus is enabled to carry out the method in accordance with claim 11, wherein the computer program product contains instructions that, when read out by the extracorporeal blood treatment apparatus, enable the extracorporeal blood treatment apparatus to carry out the method in accordance with claim 11.

17. A computer program product in accordance with claim 16, wherein the extracorporeal blood treatment apparatus has an output unit for outputting system sounds for communication with a user, the output unit is configured to transmit message sounds for communication with at least one other apparatus, and the computer program product contains instructions that, when read out by the extracorporeal blood treatment apparatus, instruct the extracorporeal blood treatment apparatus output unit to output system sounds for communication with a user, and instruct the extracorporeal blood treatment apparatus output unit to transmit message sounds for communication with at least one other apparatus.

* * * * *